(12) United States Patent
Braverman et al.

(10) Patent No.: US 6,656,168 B2
(45) Date of Patent: Dec. 2, 2003

(54) FEMININE CARE PRODUCT WITH DISCRETE AREAS OF A SKIN WELLNESS ADDITIVE

(75) Inventors: Jaime Braverman, Atlanta, GA (US); Arthur E. Garavaglia, Alpharetta, GA (US); Ali Yahiaoui, Roswell, GA (US); Robert C. Diluccio, Titusville, FL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 33 days.

(21) Appl. No.: 10/022,810

(22) Filed: Dec. 18, 2001

(65) Prior Publication Data

US 2003/0114812 A1 Jun. 19, 2003

(51) Int. Cl.⁷ ................................................ A61F 13/15
(52) U.S. Cl. ...................... 604/308; 604/387; 424/402; 424/443
(58) Field of Search .................. 604/387, 389, 604/363, 385.03, 385.04, 385.06, 289, 304, 308; 424/402, 443

(56) References Cited

U.S. PATENT DOCUMENTS

| | | | | |
|---|---|---|---|---|
| 5,643,588 A | * | 7/1997 | Roe et al. | .................... 424/402 |
| 5,843,056 A | | 12/1998 | Good et al. | |
| 5,855,999 A | | 1/1999 | McCormack | |
| 5,879,341 A | | 3/1999 | Odorzynski et al. | |
| 5,891,126 A | * | 4/1999 | Osborn et al. | ......... 604/385.17 |
| 6,149,934 A | | 11/2000 | Krzysik et al. | |
| 6,166,285 A | | 12/2000 | Schulte et al. | |
| 6,281,407 B1 | | 8/2001 | Warner et al. | |
| 6,287,581 B1 | | 9/2001 | Krzysik et al. | |
| 6,296,862 B1 | | 10/2001 | Paul et al. | |
| 6,503,524 B1 | * | 1/2003 | Tyrrell et al. | ................ 424/402 |
| 6,515,029 B1 | * | 2/2003 | Krzysik et al. | ............. 514/738 |
| 2002/0072725 A1 | * | 6/2002 | Kolby-Falk | ............ 604/385.01 |
| 2002/0077618 A1 | * | 6/2002 | Molas | ................. 604/385.201 |
| 2002/0087129 A1 | * | 7/2002 | Di Luccio et al. | .......... 604/304 |
| 2002/0099350 A1 | * | 7/2002 | Osborn, III et al. | .... 604/385.17 |
| 2002/0193758 A1 | * | 12/2002 | Sandberg | .................... 604/304 |

FOREIGN PATENT DOCUMENTS

| | | |
|---|---|---|
| EP | 0747029 A1 | 12/1996 |
| WO | 0010500 | 3/2000 |

OTHER PUBLICATIONS

U.S. patent application Publication No. 2001/0025162 A1, Sep. 27, 2001.
U.S. patent application Publication No. 2002/0138054 A1, Sep. 26, 2002.
EPO Search Report, PCT/US02/29936, Jan. 24, 2003.

* cited by examiner

Primary Examiner—Weilun Lo
Assistant Examiner—Michael G. Bogart
(74) Attorney, Agent, or Firm—Dority & Manning

(57) ABSTRACT

A feminine care absorbent article includes an outer cover and an absorbent structure in superposed relation to the outer cover and defining a bodyfacing surface. A lotion formulation is deposited on the bodyfacing surface in discrete locations targeted for specific regions of the wearer's body.

16 Claims, 4 Drawing Sheets

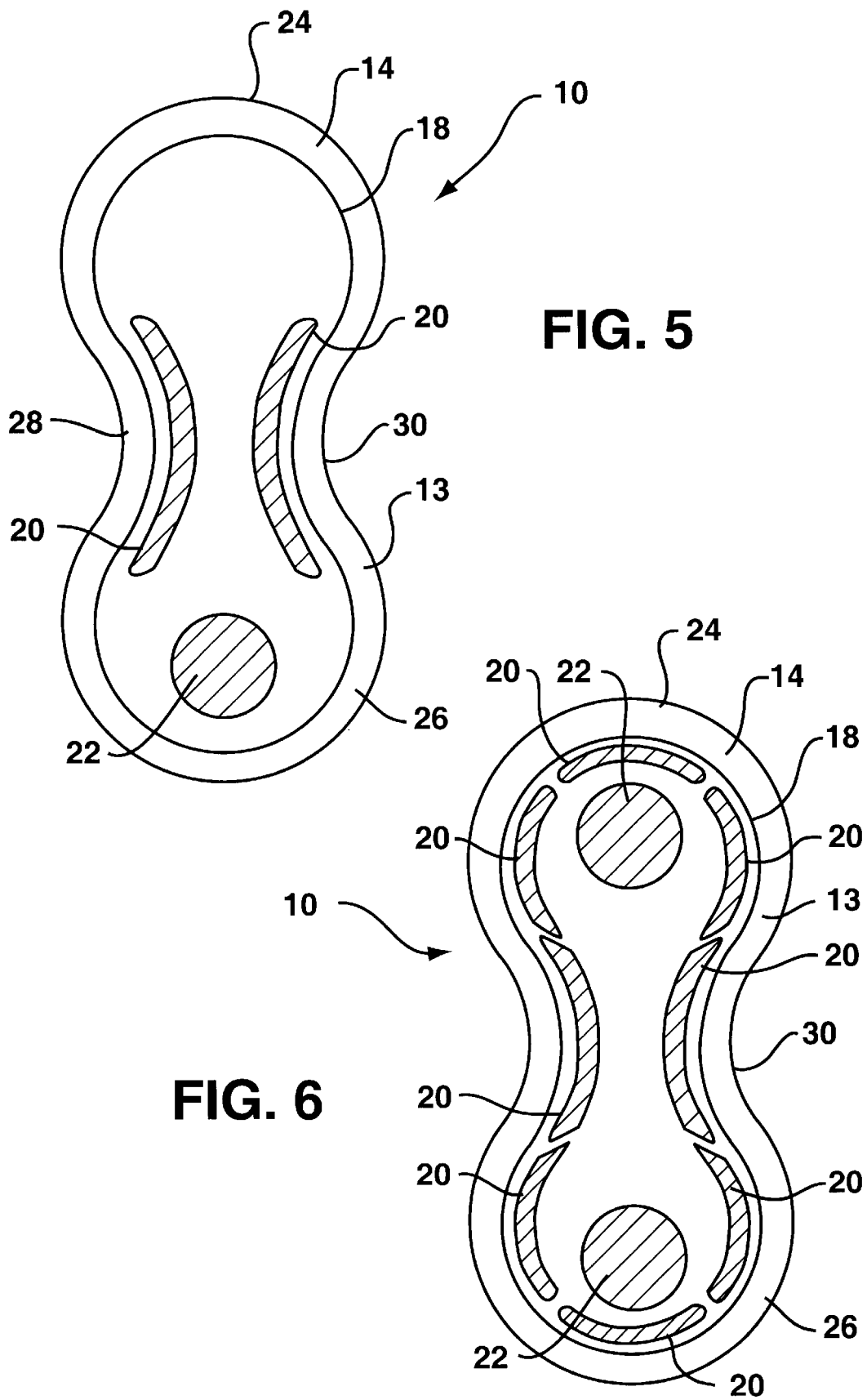

FEMININE CARE PRODUCT WITH DISCRETE AREAS OF A SKIN WELLNESS ADDITIVE

BACKGROUND OF THE INVENTION

The present invention relates generally to feminine care absorbent products such as pads and liners, and more particularly to feminine care products that improve the skin health and wellness of the wearer.

Feminine care absorbent products, such as pads and liners, are absorbent articles placed against or in proximity to a wearer's body and are designed to absorb and contain body exudates. Such articles are generally single-use or disposable items which are discarded after a relatively short period of use. The products typically include a liquid permeable bodyside liner or cover, a liquid impermeable outer cover or backsheet, and an absorbent material or structure disposed between the bodyside liner and outer cover. The liquid impermeable outer cover may be breathable, i.e., permeable to water vapor.

Although the bodyside liner that comes into contact with the wearer's skin is typically made of a soft compliant material, such as a non-woven spunbond polyolefin material, it can still abrade the skin during use and cause skin irritation and dryness. Additionally, the bodyside liner may not leave the skin completely dry of bodily fluids. Menses and other vaginal secretions can contain a variety of components that can damage the skin's outer barrier layer and lead to skin inflammation and irritation. Many wearers of feminine care products also suffer from disorders of the anorectal area, such as hemorrhoids, inflammation, chronic itching, etc. Conventional feminine care products do not address anorectal disorders and may tend to only exacerbate these disorders To reduce the likelihood of skin irritation, a wearer may apply skin protective products directly to the skin before wearing the article. Such products have included various commercially available creams and lotions. Particularly in the art of diapers and incontinence articles, it has been known to apply lotion formulations or other agents to the bodyside liner to improve skin health. In use, the lotion formulation either transfers to the skin or provides lubricity thereby reducing friction between the liner and body. Reference is made to U.S. Pat. Nos. 6,287,581 B1; 6,149,934; 6,281,407 B1. The >934 patent teaches, inter alia, that a lotion formulation may be applied to the entire surface area of an absorbent article bodyside liner or may be applied to particular sections (i.e., in a multiple stripe pattern) of the liner to provide greater lubricity of such sections.

In view of the above, it has been recognized that there is a desire and a need for improved feminine care absorbent articles that offer an improved skin wellness benefit while providing relief to anorectal disorders, and irritations or skin issues that can be caused by wearing these products.

SUMMARY

Objects and advantages of the invention will be set forth in part in the following description, or may be obvious from the description, or may be learned through practice of the invention.

The present invention provides a feminine care absorbent article, such as a pad or liner, having an outer cover, an inner bodyside liner, and an absorbent body disposed between the outer cover and bodyside liner. Discrete localized deposits of a skin wellness additive, particularly a lotion formulation, are disposed on the body facing surface of the bodyside liner. These deposits provide an increased skin wellness benefit in that they offer an enhanced degree of lubricity and protection to targeted areas of a wearer's skin. The quantity of the deposits may vary depending on the desired skin wellness benefit and may be, for example, within a range of about 0.5% to about 50% of the total weight of the bodyside liner.

In one particular embodiment, the discrete deposits are defined as longitudinally extending bands disposed along the longitudinal sides of the bodyside liner. These bands offer skin protection along the problematic sides of the liner and also may act as a liquid barrier against leakage out the sides of the article.

In another particular beneficial embodiment, the discrete deposits are defined at one or both longitudinal ends of the bodyside liner at locations targeted for the wearer's anorectal area. The term "anorectal" should be understood to not only the wearer's rectum and anus, but also the adjacent surrounding skin areas. Deposits of the lotion formulation at these target sites can provide relief to the pain, itching, and inflammation of hemorrhoids and other anorectal disorders and conditions (discomforts).

In still another embodiment, the bodyside liner is treated generally uniformly with a skin wellness additive and has additional selectively positioned deposits of lotion formulation on its surface.

In still a further embodiment, the discrete deposits of lotion formulation may include a combination of bands at the side edges and longitudinal ends of the bodyside liner, as well as at least one anorectal deposit.

The lotion formulation can vary broadly within the scope and spirit of the invention. Various formulations are widely known and used in the art for providing skin wellness benefits and to address or prevent particular skin disorders or irritating conditions. It may be desired that the lotion formulation include at least one emollient that acts as a lubricant to reduce abrasiveness of the bodyside liner against the skin and, upon transfer to the skin, helps to maintain skin condition. The emollient may be selected, for example, from the group consisting of oils, esters, glycerol esters, ethers, alkoxylated carboxylic acids, alkoxylated alcohols, fatty alcohols, and mixtures thereof. The wax selected may be natural, synthetic, or a combination thereof.

The lotion formulation may also include at least one wax selected, for example, from the group consisting of animal based waxes, vegetable based waxes, mineral based waxes, silicone based waxes, and mixtures thereof and all of which may be natural or synthetic.

The lotion formulation may also include at least one skin protectant to protect injured or exposed skin or mucous membrane surfaces from harmful or irritating stimuli.

The lotion formulation may be applied to the bodyside liner in discrete localized areas by any one of many well known manners. For example, the formulation may be sprayed or slot coated onto the liner. Other methods include rotogravure or flexographic printing.

The invention will be described in further detail below with reference to embodiments set forth in the figures.

BRIEF DESCRIPTION OF THE FIGURES

The invention will be more fully understood and further advantages will become apparent when reference is made to the following detailed description of embodiments of the invention and the accompanying drawings, in which:

FIG. 5 is a bodyside liner view of still a further embodiment of an absorbent article according to the invention;

FIG. 6 is a bodyside liner view of yet another embodiment of an absorbent article according to the invention.

DETAILED DESCRIPTION

Figure 1:
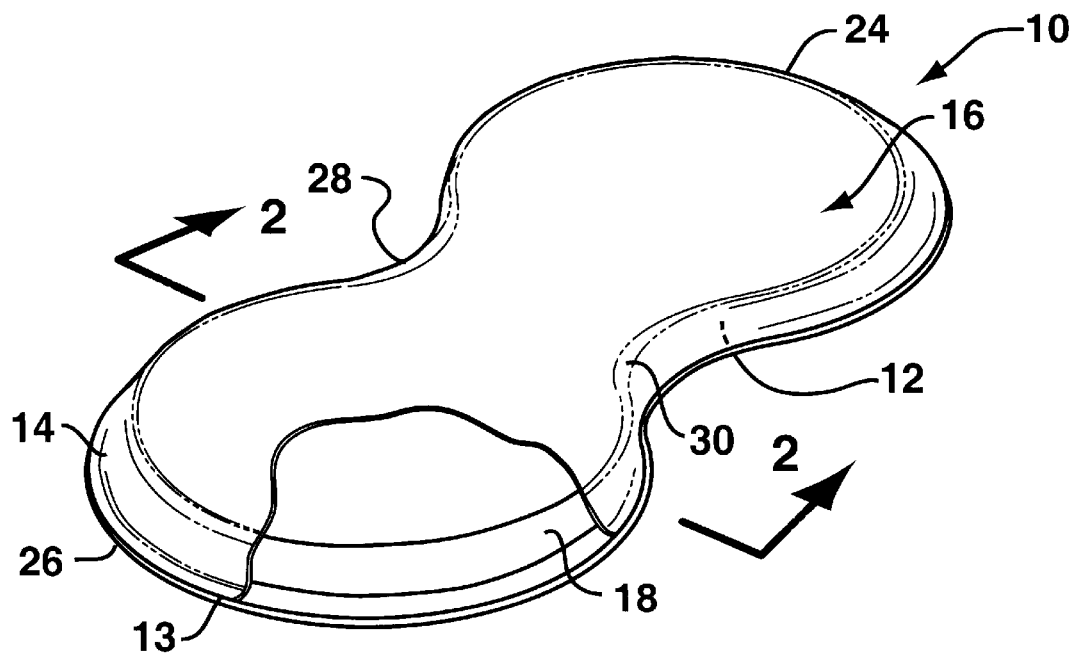
FIG. 1 is a perspective view of a typical feminine care absorbent article.

Reference will now be made in detail to one or more embodiments of the invention, examples of which are illustrated in the drawing. Each embodiment is provided by way of explanation of the invention, and not meant as a limitation of the invention. For example, features illustrated or described as part of one embodiment may be used on another embodiment to yield still a further embodiment. It is intended that the present invention include these and other modifications and variations coming within the scope and spirit of the invention.

The following description will be made in the context of feminine care absorbent articles in general. It should be appreciated that the invention is not limited to any particular type or configuration of article. For example, the invention encompasses any configuration of absorbent pad or panty liner, such as the hourglass shaped pad illustrated in the figures. Other configurations include rectangular, oval, "T" shaped, asymmetric, dog bone, and the like, and can have side protections (wings or extensions) with mechanical or adhesive attachment means.

Figure 2:
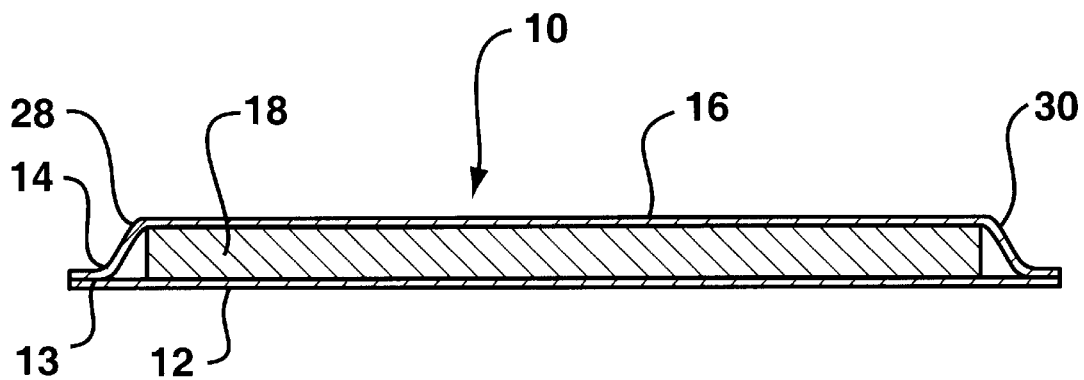
FIG. 2 is a cross-sectional view of the article of FIG. 1 taken along the lines indicated in FIG. 1.

Referring to FIGS. 1 and 2, a typical feminine care absorbent article 10, such as a pad or liner, is shown. The article 10 includes longitudinal ends 24 and 26 and opposed longitudinal sides 28 and 30, and is designed to extend through the wearer's crotch region between the legs. FIG. 2 is a cut-away view of the article 10. In this view, it can be seen that the article 10 includes a substantially liquid impermeable outer cover 12, and an absorbent structure in superposed relation to the outer cover 12. The absorbent structure may include various layers and/or components. The topmost component defines a bodyfacing surface 16 that is disposed against the wearer's skin. In the illustrated embodiment, the absorbent structure includes a porous, liquid permeable bodyside liner 14 defining the bodyfacing surface 16, and an absorbent body 18, such as an absorbent pad, disposed between the outer cover 12 and bodyside liner 14. The bodyside liner 14 is generally superimposed and coextensive with the outer cover 12, but may cover an area which is larger or smaller than the area of the outer cover 12. The body side liner 14, outer cover 12, and absorbent body 18 are integrally assembled together employing suitable attachment means, such as adhesive, sonic bonds, thermal bonds, etc. In the shown embodiment, the bodyside liner 14 and outer cover 12 are bonded together and to the absorbent body 18 with an adhesive, such as a hot melt, pressure-sensitive adhesive. The bodyside liner 14 is bonded to the outer cover 12 around the periphery of the article 10 to form a periphery margin area 13. In other embodiments, the outer cover 12 and bodyside liner 14 may have a periphery that is continuous with the edge of the absorbent body 18.

The outer cover 12 is desirably formed of a breathable material which permits vapors to escape from the absorbent body 18 while still preventing liquid exudates from passing through the outer cover 12. For example, in one particular embodiment, the outer cover 12 is formed by a microporous film/nonwoven laminate including a spunbond nonwoven material laminated to a microporous film. In another embodiment, the outer cover 12 is made of an apertured film. Suitable materials for the outer cover 12 are well known to those skilled in the art and many such materials are described, for example, in detail in U.S. Pat. No. 6,149,934. Reference is also made to U.S. Pat. No. 5,879,341; U.S. Pat. No. 5,843,056; and U.S. Pat. No. 5,855,999 for descriptions of suitable breathable materials for the outer cover 12.

The bodyside liner 14 presents the bodyfacing surface 16 which is a compliant, soft, and nonirritating to the wearer's skin. The bodyside liner 14 helps to isolate the wearer's skin from liquids held in the absorbent body 18. Further, the bodyside liner 14 may be less hydrophilic than the absorbent body 18 to present a relatively dry surface to the wearer, and may be sufficiently porous to be liquid permeable so that liquid readily penetrates its thickness to be absorbed by the absorbent body 18. A suitable bodyside liner 14 may be made from a wide selection of web materials, such as porous foams, reticulated foams, apertured plastic films, natural fibers, synthetic fibers, or any combination thereof. Various woven and nonwoven fabrics can be used for the bodyside liner 14. For example, the liner 14 may be composed of a meltblown or spunbonded web of polyolefin fibers. The bodyside liner 143 may also be a bonded-carded web of natural and/or synthetic fibers. The liner may be composed of a substantially hydrophobic material which, optionally, may be treated with a surfactant, a wetting agent, or otherwise processed to impart a desired level of wettability and hydrophilicity. The liner can be treated with a surfactant that includes a skin wellness treatment. This treatment can be applied in conjunction with the surfactant package or as a separate treatment.

The absorbent body 18 may comprise a matrix of hydrophilic fibers, such as a web of cellulosic fluff, mixed with particles of a high-absorbency material commonly known as "superabsorbent material." The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may be selectively placed into desired zones of the absorbent body 18 to better contain and absorb body exudates. Alternatively, the absorbent body 18 may include a laminate of fibrous webs and/or fibrous webs and superabsorbent materials or other suitable means of maintaining a superabsorbent material in a localized area.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body.

A hydrophilic tissue wrap sheet may be employed to help maintain the structural integrity of the absorbent body 18. The tissue wrap sheet is typically placed about the absorbent body over at least two major facing surfaces thereof and composed of an absorbent cellulosic material, such as creped wadding or a high wet-strength tissue. The tissue wrap sheet can be configured to provide a wicking layer which helps to rapidly distribute liquid over the mass of absorbent fibers constituting the absorbent body 18. Another layer can be incorporated as a surge layer or transfer layer, etc.

The absorbent article 10 according to the invention incorporates discrete localized deposits of lotion formulation on the bodyfacing surface 16 of the article, which may be, for example, the bodyfacing surface of the bodyside liner 14, as discussed in greater detail below. It should be appreciated that the invention is not limited an article having a bodyside liner 14. For example, in certain embodiments, the article may not include a liner 14 and the bodyfacing surface may be defined by an absorbent layer of material. In this case, the deposits of lotion formulation would be directly on the absorbent layer. The amount of lotion may vary widely within the scope of the invention. For example, if a bodyside liner is used, it may be desired that the lotion formulation be present at an add-on weight of between about 0.5% to about 50% of the weight of the bodyside liner 14. Although not a requirement of the invention, the lotion formulation may be substantially solid at room temperature and thus have a decreased tendency to penetrate and migrate into the bodyside liner 14 and absorbent body 18 during processing and elevated storage temperatures. It is desired that the lotion formulation remain substantially on the bodyfacing surface 16 where it can contact and transfer to the wearer's skin to provide the desired skin health benefit.

The lotion deposit(s) may be in addition to an overall skin wellness treatment applied uniformly to the bodyside liner 14. For example, the liner 14 may be treated with a surfactant that includes a skin wellness additive, or a skin wellness additive may be applied in an additional process. Any of the skin wellness additives discussed herein with respect to the lotion formulation may be applied as a separate overall treatment to the liner 14.

The invention is not limited to any particular lotion formulation. The lotion formulation may include any combination of emollients, and may also include one or more waxes. A viscosity enhancer may also be included. The lotion formulation may include other ingredients as well.

The emollient act as lubricants to reduce the abrasiveness of the bodyside liner to the skin and, upon transfer to the skin, help to maintain the soft, smooth and pliable appearance of the skin. Suitable emollients which can be incorporated into the lotion formulation include oils such as petroleum based oils, vegetable based oils, mineral oils, natural or synthetic oils, silicone oils, lanolin and lanolin derivatives, kaolin and kaolin derivatives and the like and mixtures thereof; esters such as cetyl palmitate, stearyl palmitate, cetyl stearate, isopropyl laurate, isopropyl myristate, isopropyl palmitate and the like and mixtures thereof; glycerol esters; ethers such as eucalyptol, cetearyl glucoside, dimethyl isosorbicide polyglyceryl-3 cetyl ether, polyglyceryl-3 decyltetradecanol, propylene glycol myristyl ether and the like and mixtures thereof; alkoxylated carboxylic acids; alkoxylated alcohols; fatty alcohols such as octyldodecanol, lauryl, myristyl, cetyl, stearyl and behenyl alcohol and the like and mixtures thereof; and the like and mixtures thereof. For example, a particularly well suited emollient is petrolatum. Other conventional emollients may also be added in a manner which maintains the desired properties of the lotion formulations set forth herein.

To provide the improved stability and transfer to the skin of the wearer, the lotion formulation may include from about 5 to about 95 weight percent, desirably from about 20 to about 75 weight percent, and more desirably from about 40 to about 60 weight percent of the emollient.

The wax in the lotion formulations of the present invention primarily functions as an immobilizing agent for the emollient and any active ingredient. In addition to immobilizing the emollient and reducing it's tendency to migrate, the wax in the lotion formulation provides a tackiness to the lotion formulation which improves the transfer to the skin of the wearer. The presence of the wax also modifies the mode of transfer in that the lotion tends to fracture or flake off instead of actually rubbing off onto the skin of the wearer which can lead to improved transfer to the skin. The wax may further function as an emollient, occlusive agent, moisturizer, barrier enhancer and combinations thereof.

Suitable waxes which can be incorporated into the lotion formulation include animal, vegetable, mineral or silicone based waxes which may be natural or synthetic such as, for example, bayberry wax, beeswax, C30 alkyl dimethicone, candelilla wax, carnauba, ceresin, cetyl esters, esparto, hydrogenated cottonseed oil, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, motan acid wax, motan wax, ouricury wax, ozokerite, paraffin, PEG-6 beeswax, PEG-8 beeswax, rezowax, rice bran wax, shellac wax, spent grain wax, spermaceti wax, steryl dimethicone, synthetic beeswax, synthetic candelilla wax, synthetic carnuba wax, synthetic esparto, synthetic jojoba wax, synthetic wax, and the like and mixtures thereof. For example, a particularly well suited wax includes about 70 weight percent ceresin wax, about 10 weight percent microcrystalline wax, about 10 weight percent paraffin wax and about 10 weight percent cetyl esters (synthetic spermaceti wax).

To provide the improved transfer to the skin of the wearer, the lotion formulation may include from about 5 to about 95 weight percent, desirably from about 25 to about 75 weight percent, and more desirably from about 40 to about 60 weight percent of the wax. Lotion formulations which include an amount of wax less than the recited amounts tend to have lower viscosities which undesirable leads to migration of the lotion. Whereas, lotion formulations which include an amount of wax greater than the recited amounts tend to provide less transfer to the wearer's skin.

A viscosity enhancer may be added to the lotion formulation to increase the viscosity to help stabilize the formulation on the bodyfacing surface 16 of the bodyside liner 14 and thereby reduce migration and improve transfer to the skin. Desirably, the viscosity enhancer increases the viscosity of the lotion formulation by at least about 50 percent, more desirably at least about 100 percent, even more desirably by at least about 500 percent, yet even more desirably by at least about 1000 percent, and even more desirably by at least about 5000 percent. Suitable viscosity enhancers which can be incorporated into the lotion formulation include polyolefin resins, lipophilic/oil thickeners, ethylene/vinyl acetate copolymers, polyethylene, silica, talc, colloidal silicone dioxide, zinc stearate, cetyl hydroxy ethyl cellulose and other modified celluloses and the like and mixtures thereof. For example, a particularly well suited viscosity enhancer is an ethylene/vinyl acetate copolymer commercially available from E.I. Dupont De Ne Mours, a business having offices located in Wilmington, Del. under the trade designation ELVAX.

To provide the improved transfer to the skin of the wearer, the lotion formulation may include from about 0.1 to about 25 weight percent, desirably from about 5 to about 20 weight percent, and more desirably from about 10 to about 15 weight percent of the viscosity enhancer for reduced migration and improved transfer to the wearer's skin.

If it is desired that the lotion formulation treat the skin, it can also include an active ingredient such as a skin protectant. Skin protectants may be a drug product which protects injured or exposed skin or mucous membrane surface from harmful or irritating stimuli. Suitable active ingredients, in addition to those mentioned above as suitable emollients, which can be incorporated into the lotion formulation include, but are not limited to, alantoin and its derivatives, aluminum hydroxide gel, calamine, cocoa butter, dimethicone, cod liver oil, glycerin, kaolin and its derivatives, lanolin and its derivatives, mineral oil, shark liver oil, talc, topical starch, zinc acetate, zinc carbonate, and zinc oxide and the like, and mixtures thereof. The lotion formulation may include from about 0.10 to about 95 weight percent of the active ingredient depending upon the skin protectant and the amount desired to be transferred to the skin.

In order to better enhance the benefits to the wearer, additional ingredients can be included in the lotion formulations of the present invention. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); astringents—cosmetic (induce a tightening or tingling sensation on skin); astringent—drug (a drug product which checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); other emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal), silicones/organomodified silicones (protection, tissue water resistance, lubricity, tissue softness), oils (mineral, vegetable, and animal),; natural moisturizing agents (NMF) and other skin moisturizing ingredients known in the art; opacifiers (reduce the clarity or transparent appearance of the product); powders (enhance lubricity, oil adsorption, provide skin protection, astringency, opacity, etc.); skin conditioning agents; solvents (liquids employed to dissolve components found useful in the cosmetics or drugs); and surfactants (as cleansing agents, emulsifying agents, solubilizing agents, and suspending agents).

Figure 3:
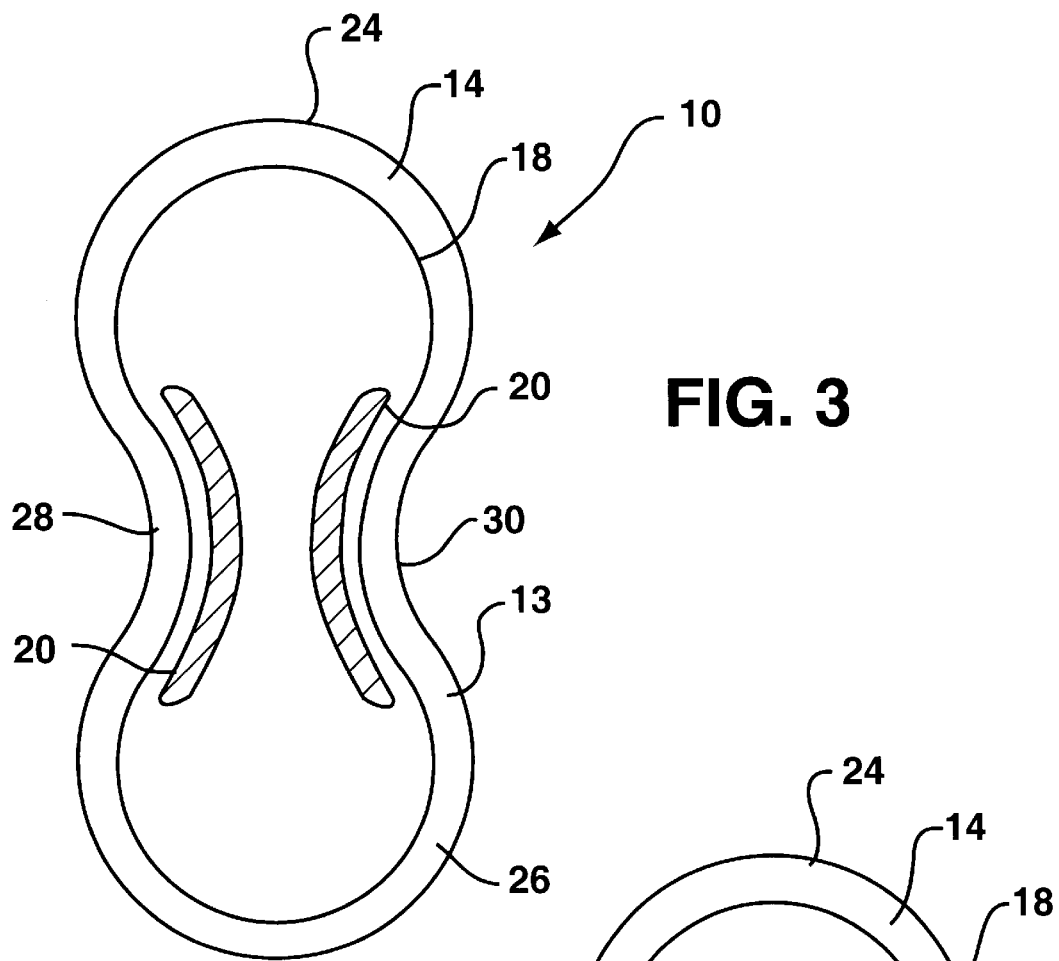
FIG. 3 is a bodyside liner view of an embodiment of an absorbent article according to the invention.

As mentioned, the lotion deposits 20 are provided as discrete localized deposits on the bodyfacing surface 16 of the article. The locations of the deposits 20 are chosen to target particular problem areas. FIGS. 3 through 6 illustrate various embodiments of strategically targeted lotion deposits 20. FIG. 3 shows an embodiment wherein the lotion deposits are defined as generally longitudinally extending bands disposed along opposite longitudinal sides 28 and 30 of the bodyside liner 14. For certain users, the longitudinal side regions of absorbent articles are particularly problematic in that they tend to chafe the skin resulting in irritation and general discomfort. The longitudinally extending bands of lotion deposits 20 will help alleviate this problem by lubricating the skin in contact with the side regions. The bands 20 also provide the additional benefit of fluid barrier protection along the sides of the absorbent article 10 where leakage is a particular concern. Although the bands 20 are illustrated as continuous in the drawings, it should be appreciated that the bands may also include a discontinuous pattern of deposits, such as illustrated in FIG. 6.

Figure 4:
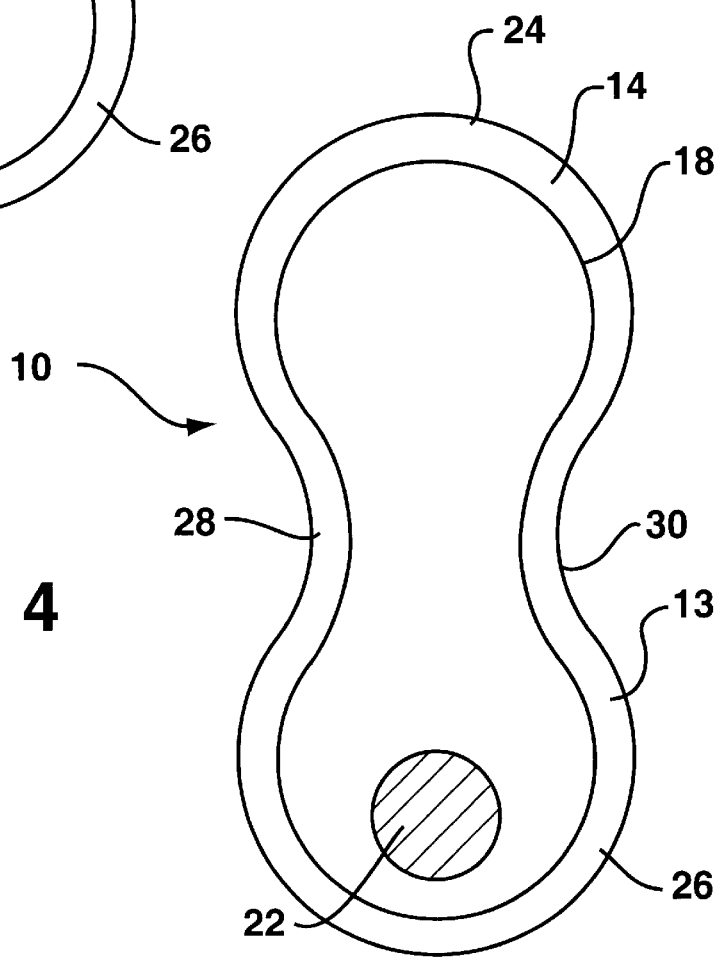
FIG. 4 is a bodyside liner view of an alternate embodiment of an absorbent article according to the invention.

FIG. 4 illustrates an embodiment wherein the discrete lotion deposit is at a longitudinal end 26 of the article 10 and specifically intended as an anorectal deposit 22. This deposit 22 is specifically targeted for the user's anorectal area and the lotion formulation may be specifically chosen to alleviate any number of anorectal disorders and discomforts, including hemorrhoids, itching, swelling, etc. The absorbent article 10 according to this embodiment thus serves the dual purpose of a feminine care absorbent article and an anorectal area treatment device. In the illustrated embodiment, the anorectal deposit 22 is an "island-like" deposit in that it is completely localized and surrounded by bodyside liner 14. However, it should be appreciated that any deposit configuration may be utilized for specific targeting of the user's anorectal area. For example, it may be that an entire longitudinal end portion of the liner 14 is coated with a lotion deposit 20 for this purpose. Different lotions for specific anorectal and skin issues can be placed in the surface area of the body side liner. Depending on the product design, it can be elected that each lotion treatment placed in the product might have another formulation for specific skin issues that each region can have.

So that a user need not determine which end of the absorbent article 10 contains the anorectal lotion deposit 22, particularly with symmetrically shaped articles, it may be desired to include an anorectal lotion deposit 22 at both longitudinal ends 24 and 26 of the article 10. In this manner, the user can orient the article in either longitudinal direction.

FIG. 5 illustrates an embodiment wherein the lotion deposits are a combination of an anorectal deposit 22 and longitudinally extending side bands 20.

FIG. 6 illustrates an embodiment wherein an anorectal deposit 22 is provided at each longitudinal end 24 and 26 of the article 10 and band deposits 20 are disposed generally around the perimeter of the liner 14. The band deposits 20 lubricate and protect the skin around the entire circumference of the article 10 and the anorectal deposits 22 provide a health benefit to the user's anorectal area.

Figure 7:
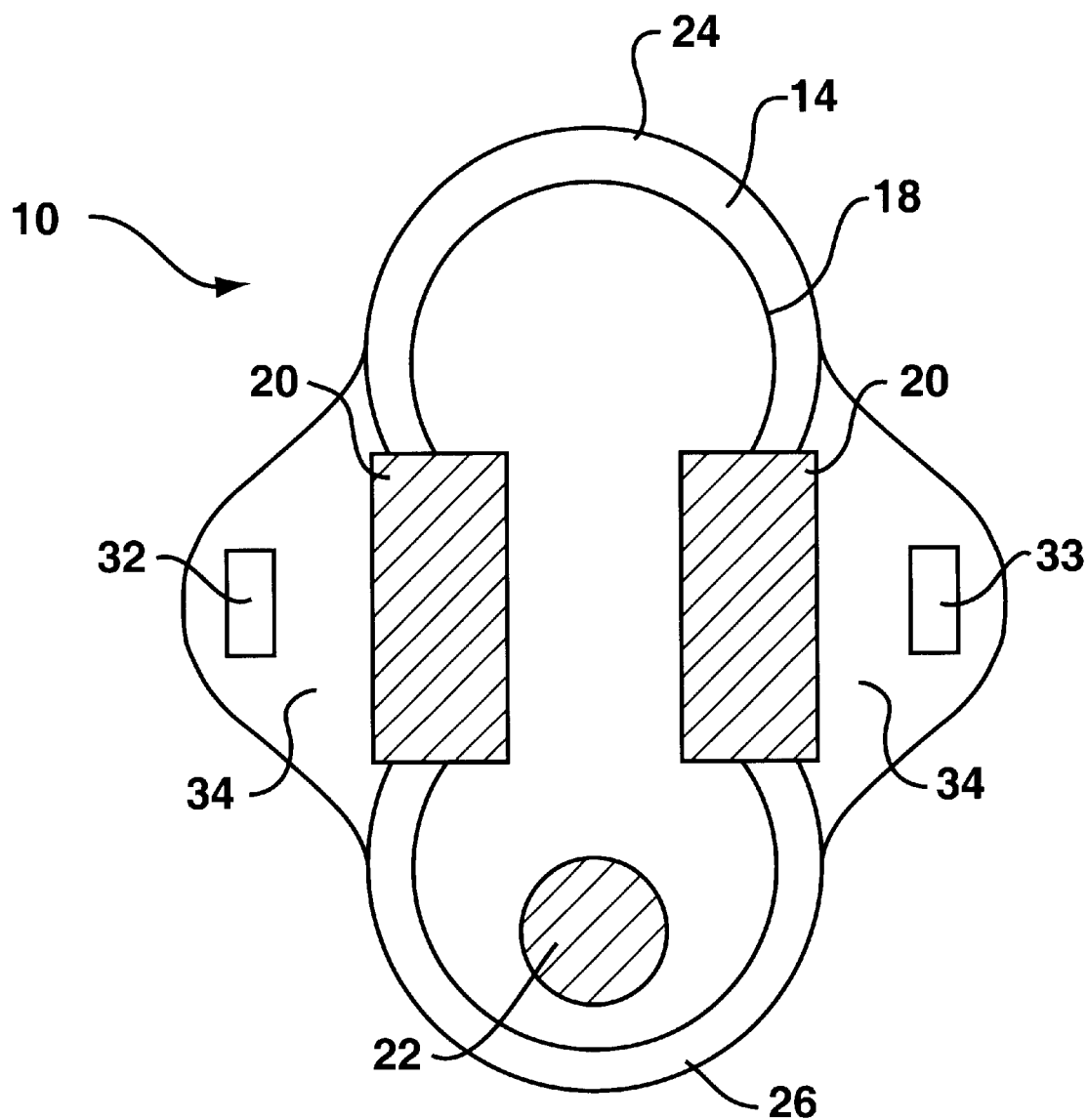
FIG. 7 is a bodyside liner view of another embodiment of an absorbent article according to the invention.

FIG. 7 illustrates an embodiment wherein the article 10 includes protective side portions or "wings" 34. The lotion deposits 20 are provided at the sides of the article 10 and extend onto the wings 34. An anorectal deposit 22 is also provided. Conventional adhesive attachment tabs are provided on the wings 34 for securing the wings in place during use of the article 10.

It should be appreciated by those skilled in the art that various modifications and variations can be made to the embodiments of the invention described herein without departing from the scope and spirit of the invention. It is intended that the present invention include such modifications and variations and come within the scope of the appended claims.

What is claimed is:

1. A feminine care absorbent article, comprising:
an outer cover;
an absorbent structure in superposed relation to said outer cover, said structure defining a bodyfacing surface;
a lotion formulation deposited on said body facing surface in at least one discrete location targeted for a specific body region of a wearer, said lotion formulation designed to address a skin health issue that is particular to the targeted body region;
wherein said absorbent structure comprises a liquid permeable bodyside liner defining said bodyfacing surface, and an absorbent body disposed between said bodyside liner and said outer cover;
wherein said lotion formulation is deposited in a discrete location on an area of said bodyfacing surface targeted specifically for the wearer's anorectal area; and
wherein said anorectal discrete lotion deposit comprises an island-like deposit at one longitudinal end of said bodyfacing surface such that a wearer positions said longitudinal end adjacent the anorectal area.

2. The feminine care absorbent article as in claim 1, further comprising an additional island-like deposit of said lotion formulation at an opposite longitudinal end of said bodyfacing surface such that a wearer can position either said longitudinal end adjacent the anorectal area.

3. A feminine care absorbent article, comprising:
an outer cover;
an absorbent structure in superposed relation to said outer cover, said structure defining a bodyfacing surface;
a lotion formulation deposited on said body facing surface in at least one discrete location targeted for a specific body region of a wearer, said lotion formulation designed to address a skin health issue that is particular to the targeted body region;
wherein said absorbent structure comprises a liquid permeable bodyside liner defining said bodyfacing surface, and an absorbent body disposed between said bodyside liner and said outer cover; and
wherein said discrete lotion deposits comprise longitudinally extending bands along opposite sides of said bodyfacing surface, said bands having an overall shape corresponding generally to medial contours of said absorbent article between longitudinal end portions of said absorbent article.

4. A feminine care absorbent article, comprising:
an outer cover;
an absorbent structure in superposed relation to said outer cover, said structure defining a bodyfacing surface;
a lotion formulation deposited on said body facing surface in at least one discrete location targeted for a specific body region of a wearer, said lotion formulation designed to address a skin health issue that is particular to the targeted body region;
wherein said absorbent structure comprises a liquid permeable bodyside liner defining said bodyfacing surface, and an absorbent body disposed between said bodyside liner and said outer cover; and
wherein said discrete lotion deposits are disposed around a perimeter of said bodyfacing surface liner.

5. A feminine care absorbent article, comprising:
an outer cover
a liquid permeable bodyside liner connected in superposed relation to said outer cover, said bodyside liner having a body facing surface;
an absorbent body disposed between said bodyside liner and said outer cover;
a lotion formulation deposited on said body facing surface of said bodyside liner in discrete locations; and
wherein said discrete locations comprise longitudinally extending bands disposed along opposite side edges of said bodyside liner, said bands providing a skin health benefit and further providing fluid barrier protection against leakage along sides of said absorbent article.

6. The feminine care absorbent article as in claim 5, wherein said longitudinally extending bands are continuous along said side edges.

7. The feminine care absorbent article as in claim 5, wherein said longitudinally extending bands are discontinuous along said side edges.

8. The feminine care absorbent article as in claim 5, wherein said discrete deposits of lotion formulation further comprise bands disposed at longitudinal ends of said bodyside liner.

9. The feminine care absorbent article as in claim 5, wherein said discrete deposits of lotion formulation comprise at least one deposit at a longitudinal end of said bodyside liner at a location targeted for the anorectal location of a wearer.

10. The feminine care absorbent article as in claim 9, further comprising a discrete deposit of lotion formulation at each longitudinal end of said bodyside liner at locations targeted for the anorectal location of a wearer so that said article can be worn in either longitudinal orientation.

11. The feminine care absorbent article as in claim 5, wherein said lotion formulation comprises an emollient.

12. The feminine care absorbent article as in claim 5, wherein said lotion formulation comprises a skin protectant agent.

13. The feminine care absorbent article as in claim 5, wherein said lotion formulation comprises a wax.

14. The feminine care absorbent article as in claim 5, wherein said lotion formulation comprises a combination of at least one emollient, at least one skin protectant agent, and at least one wax.

15. The feminine care absorbent article as in claim 5, wherein said bodyside liner is also treated generally uniformly with a skin wellness treatment additive.

16. The feminine care absorbent article as in claim 5, further comprising protective wing portions, said bands of lotion formulation extending at least partially onto said wing portions.

* * * * *